(12) United States Patent
Weng et al.

(10) Patent No.: US 9,545,209 B2
(45) Date of Patent: Jan. 17, 2017

(54) VCG VECTOR LOOP BIFURCATION

(71) Applicant: ZOLL Medical Corporation, Chelmsford, MA (US)

(72) Inventors: Binwei Weng, Chelmsford, MA (US); Ulrich Herken, Medford, MA (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 14/628,525

(22) Filed: Feb. 23, 2015

(65) Prior Publication Data

US 2015/0238101 A1   Aug. 27, 2015

Related U.S. Application Data

(60) Provisional application No. 61/945,424, filed on Feb. 27, 2014.

(51) Int. Cl.
*A61B 5/04* (2006.01)
*A61N 1/39* (2006.01)
*A61B 5/00* (2006.01)

(52) U.S. Cl.
CPC ............ *A61B 5/04011* (2013.01); *A61N 1/39* (2013.01); *A61B 5/0006* (2013.01); *A61N 1/3925* (2013.01); *A61N 1/3956* (2013.01)

(58) Field of Classification Search
CPC . A61B 5/0402; A61B 5/7235; A61B 5/04011; A61B 5/0452; A61B 5/05; A61B 5/0245; A61B 5/7264; A61B 5/0006; A61B 5/00; A61B 5/0044; A61B 5/04; A61B 5/4836; A61B 5/04012; A61B 5/4848; A61B 5/486;A61B 5/7275; A61N 1/3925; A61N 1/3937; A61N 1/3702; G06F 19/3437; G06F 19/34; G06F 19/345; Y10S 128/92; Y10S 128/923; Y10S 128/924
See application file for complete search history.

(56) References Cited

U.S. PATENT DOCUMENTS

| | | | |
|---|---|---|---|
| 6,366,870 B2 | 4/2002 | Jarman et al. | |
| 6,579,242 B2 | 6/2003 | Bui et al. | |
| 6,993,377 B2 | 1/2006 | Flick et al. | |
| 7,123,954 B2 | 10/2006 | Narayam et al. | |
| 2007/0032733 A1 | 2/2007 | Burton | |
| 2012/0226178 A1 | 9/2012 | Freeman et al. | |

OTHER PUBLICATIONS

Burch, George E., "The History of Vectorcardiography," (1985) Medical History, vol. 29, Supplement 5, pp. 103-131.

(Continued)

*Primary Examiner* — Deborah Malamud
(74) *Attorney, Agent, or Firm* — Fish & Richardson P.C.

(57) ABSTRACT

A system for determining T wave bifurcation that includes three or more ECG leads configured to receive an ECG signal and a first computing device including a processor coupled to a memory, the processor and the memory configured to perform operations including: generating at least two orthogonal ECG vectors based on the ECG signal of a patient, processing the at least two orthogonal ECG vectors to determine a loop trajectory of at least a portion of the ECG signal, identifying a trajectory bifurcation by comparing the loop trajectory to a control loop trajectory for a plurality of cardiac cycles, and determining an indicator of a cardiac event based on the trajectory bifurcation.

18 Claims, 11 Drawing Sheets

(56) References Cited

OTHER PUBLICATIONS

An example of Mann's graphing from *Hubert Mann, 'A method of analyzing the electrocardiogram', Arch. intern. Med.*, 1920,25: 283-294.
International Search Report & Written Opinion, PCT/US2015/17050, mailed May 22, 2015, 13 pages.
Ragheb, Hossein, et al., "Quantitative shape analysis with weighted covariance estimates for increased statistical efficiency," Frontiers in Zoology 2013, 10:16, 24 pages.

VCG VECTOR LOOP BIFURCATION

CLAIM OF PRIORITY

This application claims priority under 35 USC §119(e) to U.S. Patent Application Ser. No. 61/945,424, filed on Feb. 27, 2014, the entire contents of which are hereby incorporated by reference.

TECHNICAL FIELD

This document relates to identification and management of patients at risk of cardiac events, and in particular to systems and techniques for determining T wave bifurcation.

BACKGROUND

The most common tool used for cardiac diagnosis is based on electrocardiogram (ECG) measurement and interpretation. Traditional ECG includes information about the timing of cardiac electrical events and the time intervals between two or more such events. For example, transmural repolarization, reflected by the T wave in an ECG, can indicate a plurality of abnormalities that mark susceptibility to life-threatening arrhythmias. Such abnormalities can be associated with genetic defects, various acquired cardiac dysfunctions, electrolyte disorders, and certain prescription and non-prescription drugs.

SUMMARY

In a general aspect, a system includes three or more ECG leads configured to receive an ECG signal from a patient and a first computing device including a processor coupled to a memory. The processor and the memory are configured to perform operations including: generating at least two orthogonal ECG vectors based on the ECG signal of a patient, processing the at least two orthogonal ECG vectors to determine a loop trajectory of at least a portion of the ECG signal, identifying a trajectory bifurcation by comparing the loop trajectory to a control loop trajectory for a plurality of cardiac cycles, and determining an indicator of a cardiac event based on the trajectory bifurcation.

Embodiments can include one or more of the following features.

The loop trajectory is a test loop trajectory that includes a first plurality of loop trajectories obtained during a first time period and the control loop trajectory includes a second plurality of loop trajectories obtained during a second time period that is prior to the first time period.

The first time period includes a time period in present or recent past and the second time period includes a time period in a more distant past. The first time period includes a time period within 60 minutes of a present time and the second time period includes a time period within 72 hours of the present time. The first time period and the second time period are separated by at least 5 minutes.

The portion of the ECG signal includes a QRS wave. The portion of the ECG signal includes at least one of a T wave, a P wave and an S wave.

The identification of the trajectory bifurcation further includes measuring a degree of trajectory bifurcation between the loop trajectory and the control loop trajectory. The measurement of the degree of the trajectory bifurcation is based on a statistical analysis. The statistical analysis is a non-Gaussian statistical analysis.

The cardiac event includes an impending acute degeneration of a patient's medical condition. The impending acute degeneration is one of a cardiac arrest and a traumatic arrest.

The identification of the trajectory bifurcation further includes identifying landmarks in the loop trajectory and in the control loop trajectory. The identification of the trajectory bifurcation further includes determining a measure of a shape uncertainty of the loop trajectory and the control loop trajectory. Determining the measure of the shape uncertainty is based on a statistical analysis of an uncertainty boundary of the loop trajectory and the control loop trajectory.

The first computing device includes a defibrillator. The first computing device includes a mobile computing device. The first computing device is configured to transmit the indicator of the cardiac event to a defibrillator.

In a general aspect, an apparatus includes a computer readable medium storing instructions for causing a computing system to perform operations including: receiving, from two or more ECG leads, an ECG signal of a patient, generating at least two orthogonal ECG vectors based on the ECG signal, processing the at least two generally orthogonal ECG vectors to determine a loop trajectory of at least a portion of the ECG signal, identifying a trajectory bifurcation by comparing the loop trajectory to a control loop trajectory for a plurality of cardiac cycles and determining an indicator of a cardiac event based on the trajectory bifurcation.

Embodiments may include one or more of the following features.

The cardiac event includes an impending acute degeneration of a patient's medical condition. The impending acute degeneration is one of a cardiac arrest and a traumatic arrest. The apparatus is a defibrillator. The defibrillator performs operations including delivering a treatment to the patient based on the indicator of a cardiac event.

In a general aspect, a computer-implemented method executed by one or more processors includes: receiving, from two or more ECG leads, an ECG signal, generating at least two orthogonal ECG vectors based on the ECG signal, processing the at least two generally orthogonal ECG vectors to determine a loop trajectory of at least a portion of the ECG signal, identifying a trajectory bifurcation by comparing the loop trajectory to a control loop trajectory for a plurality of cardiac cycles, and determining an indicator of a cardiac event based on the trajectory bifurcation.

Embodiments may include one or more of the following features.

Processing the at least two orthogonal ECG vectors to determine a loop trajectory includes: detecting an onset of a portion of the ECG signal and an end of the portion of the ECG signal, isolating the portion of the ECG signal based on detecting the onset of the portion of the ECG signal and an end of the portion of the ECG signal, and generating a vector loop based of the portion of the ECG signal.

The identification of the trajectory bifurcation includes calculating an area of the loop trajectory and subtracting the area of the loop trajectory from an area of the control loop trajectory. The identification of the trajectory bifurcation further includes: comparing the trajectory bifurcation of at least three consecutive cardiac cycles of the plurality of cardiac cycles, determining a trend of the trajectory bifurcation and based on the trend, defining an episodic trajectory bifurcation.

The techniques described herein can have one or more of the following advantages. The systems and methods described herein provide a software analytic tool that provides an accurate prediction of impending acute degeneration of a patient's medical condition. The software analytic tool can automatically analyze VCG loops of patients to non-invasively detect and predict pending cardiac conditions that can constantly change over time. In some examples, a trajectory bifurcation can be identified based on comparison of a loop trajectory to previously stored control loop trajectories (e.g., a control loop generated based on an averaging of several prior loop trajectories). For example, a system can generate three orthogonal ECG vectors based on ECG data. By processing the orthogonal vectors, a loop trajectory can be determined and compared to a stored control loop trajectory. Differences in the loop trajectories can be used to identify trajectory bifurcation. A trend of differences observed over time allows a caregiver to view information about the patient's cardiac rhythm at any point in time, which can aid in diagnosing and treating the patient. For instance, re-displaying a portion of the patient's ECG trace from a point in time when treatment was started and/or a portion of the patient's ECG trace prior to receiving a treatment can provide information that can be used to diagnose the patient's condition. Knowledge of the patient's likely diagnosis can inform treatment of the patient, both at a rescue scene and in a hospital setting. The ability to view the historical information about treatment and health status of the patient at the rescue scene or at another location, such as at a hospital, can enable skilled caregivers to make informed treatment decisions even if those caregivers were not present when the information was recorded.

It is appreciated that methods in accordance with the present disclosure can include any combination of the aspects and features described herein. That is to say that methods in accordance with the present disclosure are not limited to the combinations of aspects and features specifically described herein, but also include any combination of the aspects and features provided.

The details of one or more embodiments are set forth in the accompanying drawings and the description below. Other features and advantages will be apparent from the description, drawings, and claims.

DETAILED DESCRIPTION

Implementations of the present disclosure are generally directed to systems and methods for measuring a degree of trajectory bifurcation and determining an impending acute degeneration of a patient's medical condition based on the degree of trajectory bifurcation. The measurement of the trajectory bifurcation can include identifying, viewing and analyzing T wave alternans (TWA).

Figure 1:
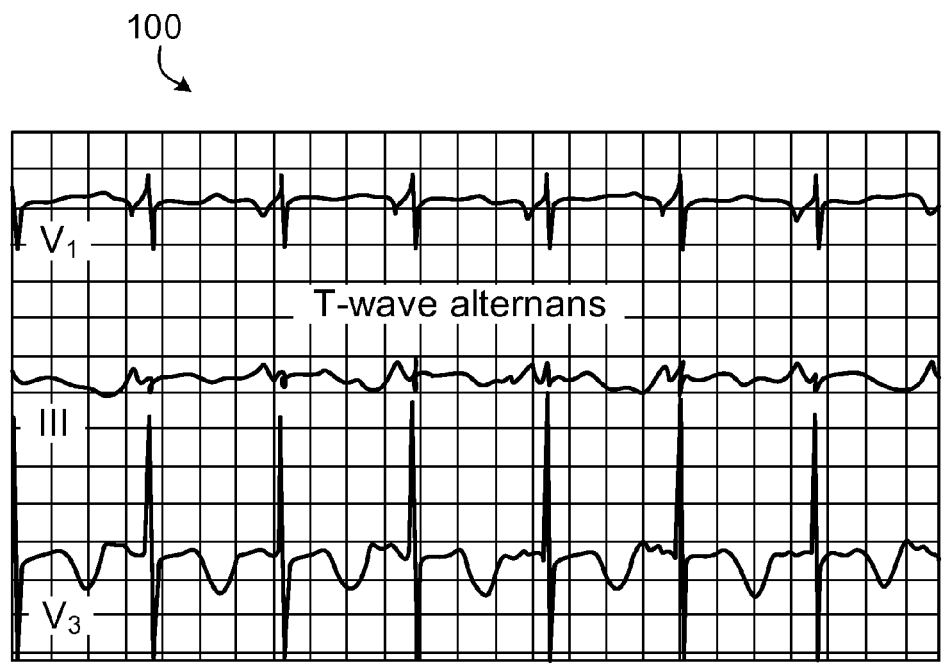
FIG. 1 is a graphical example of T-wave alternans and prolonged QT interval.

T wave alternans (TWA) represent periodic beat-to-beat variations in the amplitude or shape of the T wave in an electrocardiogram (ECG or EKG). FIG. 1 shows a graphical example of TWA and prolonged QT interval 100. TWA can include large variations ("macroscopic" TWA) that are associated with increased susceptibility to lethal ventricular tachycardias. TWA can also include microvolt T wave alternans (MTWA) that are variants of TWA and are associated with an increased risk of sudden cardiac death. MTWA can be used in patients who have had myocardial infarctions (heart attacks) or other heart damage to see if they are at high risk of developing a potentially lethal cardiac arrhythmia. The patients identified to be at high risk can potentially benefit from the placement of a defibrillator device, which can stop an arrhythmia and save the patient's life.

The TWA test uses an electrocardiogram (ECG) measurement of the heart's electrical conduction. The test looks for the presence of repolarization alternans (e.g., TWA), which is a variation in the vector and amplitude of the T wave component of the ECG. The amount of variation is small, on the order of microvolts. A small variation in the vector and amplitude of the T wave component can be detected by digital signal processing techniques.

MTWA detects T wave alternans signals as small as one-millionth of a volt. Microvolt T wave alternans is an alternation in the morphology of the T wave in every other beat or AB-AB pattern. MTWA is associated with ventricular arrhythmias and sudden death. In some cases, visually discernible alternans have been linked to the rapid onset of ventricular tachyarrhythmias. In some examples, visually indiscernible alternans can also be significant.

Figure 2:
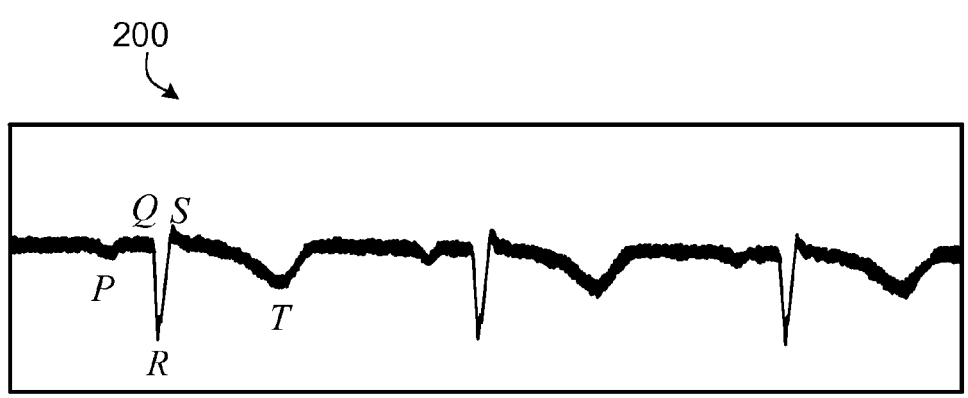
FIG. 2 is a graphical example of a mean vector of the QRS complex as projected on to the frontal plane.

The presence of alternans can be determined using various mathematical tools and concepts including vector and loop analysis. For example, electric forces from the heart as recorded from the body surface can be represented as a vector force. The equilateral triangle of Einthoven can be used to obtain the mean electric axis of the QRS complex of the recorded electrocardiogram from standard limb leads I, II, and III. FIG. 2 illustrates an example mean vector 200 as projected on to the frontal plane. The angle of the vector indicates the direction of the mean vector 200, and its length indicates the mean magnitude. The quantities of the mean vector, including the direction and the magnitude, as projected on the frontal plane also indicate a "sense." The "sense" indicated by the vector can be described by the fact that the vector is directed away from the area of greatest relative negativity of the electric force derived from the heart toward the area of greatest relative positivity.

Figure 3:
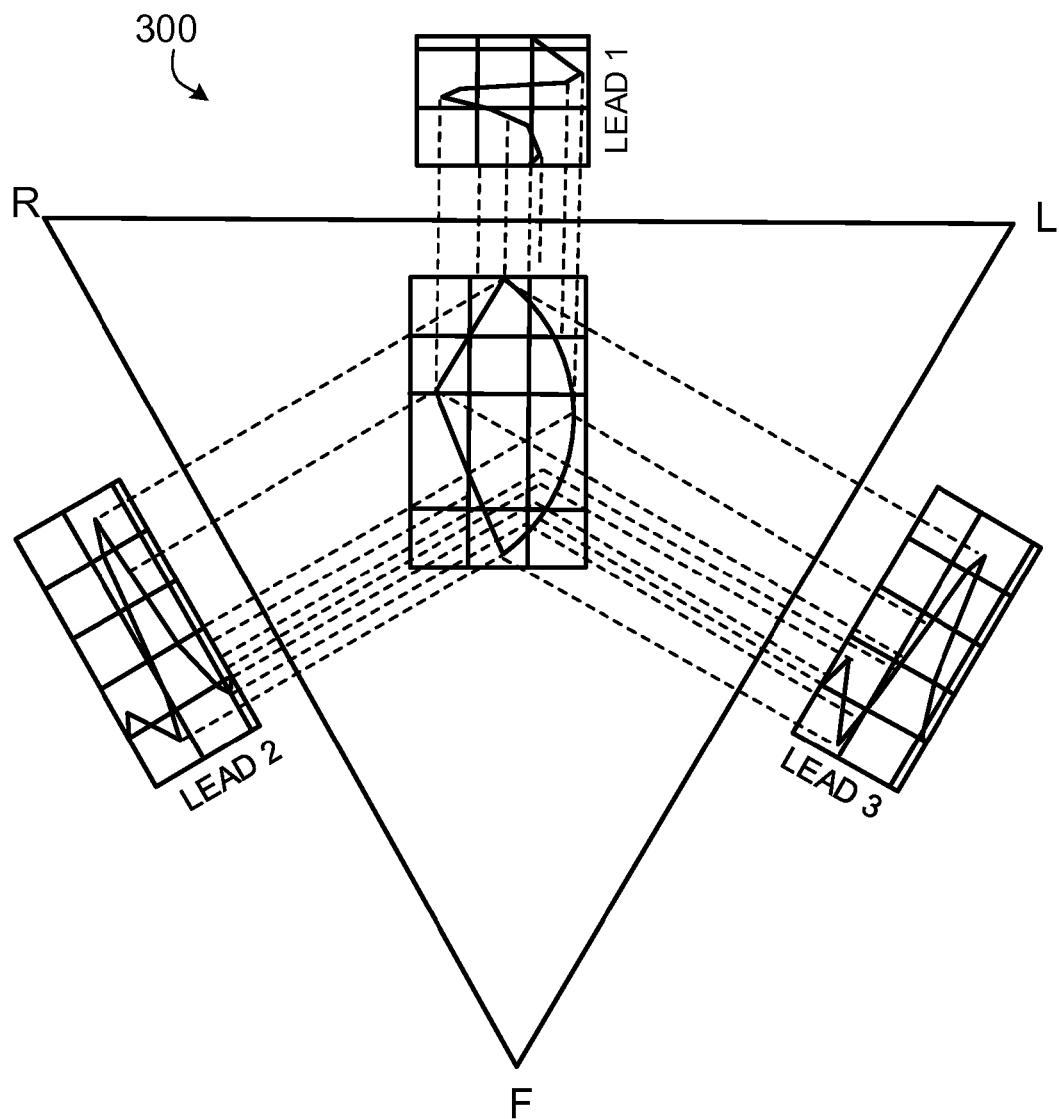
FIG. 3 is a graphical example of a monocardiogram.

As another example, electric forces from the heart as recorded from the body surface can be represented as a "loop." The loop can be defined as a continuous uninterrupted series of vectors that are displayed as vector quantities of the electric forces of cardiac depolarization and repolarization recorded by the electrocardiogram. An example of a series of vectors 300 used for vector analysis, as graphed by Hubert Mann, is shown in FIG. 3.

Various lead configurations can be used to measure and analyze electrical events. In some situations, three leads can be designed to record components of a resultant cardiac electromotive force in three mutually perpendicular directions, then the problem of deriving the resultant cardiac electromotive force is solved. For example, suppose that the potential measured by any electrocardiographic lead is represented by V and that the resultant cardiac electromotive force is denoted by H or, as it is sometimes known, the "heart vector." From mathematical considerations, it can be shown that V=H·L, where L is the vector representing the strength of the lead being used to measure the potential. The mathematical formula of the cardiac potential can be expanded to the following: $V=H_xL_x+H_yL_y+H_zL_z$, where $H_x$, $H_y$, $H_z$ are the three components of the heart vector and $L_x$, $L_y$, $L_z$ are the three components of the lead vector. The mathematical formula of the cardiac potential indicates that the component of the heart vector in the X direction can be measured and a lead can be designed to have components (Lx, 0, 0). For an X-direction measurement, the potential can be expressed as $V_x=H_xL_x$, and if the strength $L_x$ of the lead is known, then when the potential $V_x$ can be measured and $H_x$ can be calculated.

Over the years, a number of different electrode configurations have been developed that provide a method of generating at least two orthogonal leads, though mostly the full X, Y, and Z orthogonal leads of VCG are used. Some examples of electrode configurations are the Grishman, Milnor, Wilson-Burch, Frank, Dower and the standard 12 lead configuration well-known in clinical practice from which the orthogonal lead set can be derived. The "orthogonal" leads can be approximations of truly orthogonal leads. The term orthogonal leads can be a practical, broader approximation of orthogonal leads, including truly orthogonal leads as a subset.

Vectorcardiography has been supplanted by the 12 lead ECG because the loops generated by the VCG are too complex for even highly trained cardiologists to fully comprehend. In vectorcardiography (VCG), myocardial electrical activity is treated mathematically as a dipole that is the aggregate of the electrical activity of all the cells of the myocardium. The dipole size and spatial angle are presented as a vector whose angle and magnitude change during a cardiac cycle. For example, in VCG, the measurement points are positioned in such a way that three derived signals correspond to three orthogonal axes (X, Y, Z).

Figure 4:
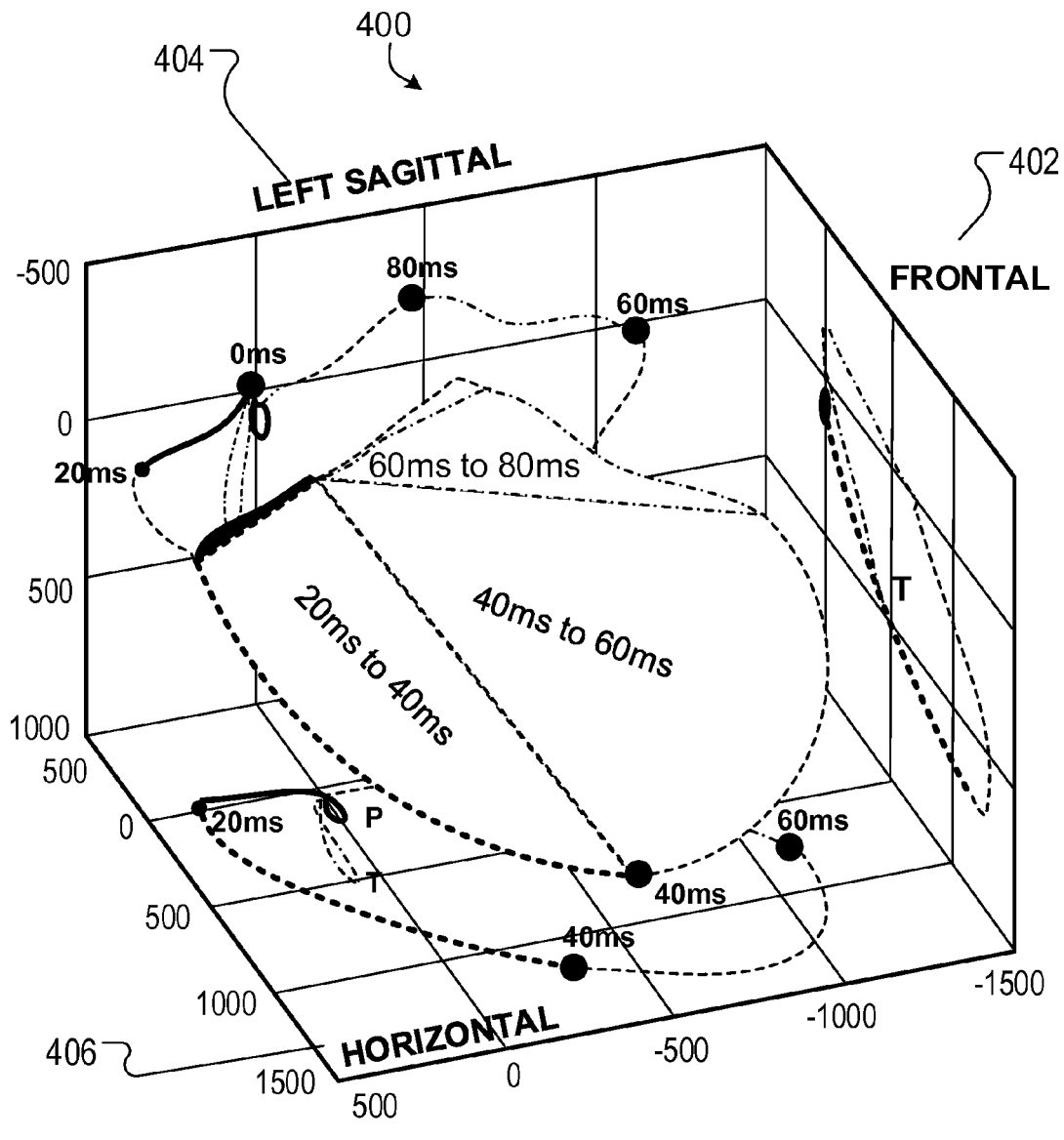
FIG. 4 is a graphical example of a vector of the VCG and its motion presented as projections of the vectorcardiograph onto one or more planes.
Figure 4:
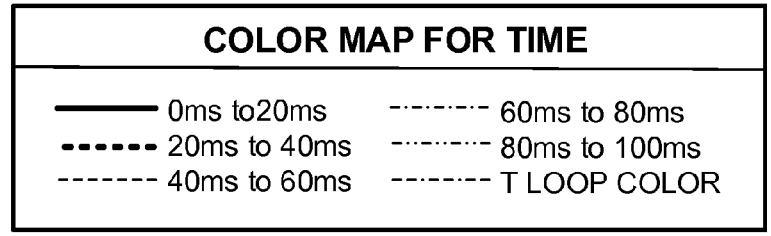

The VCG can be conceptualized as the trajectory of the "tip" of the representative vector in the two or three-dimensional measurement space. In some embodiments, the VCG represents the ECG as a the motion of a three dimensional vector, but it can be easily understood by those skilled in the art that the representation can be formed in a bidimensional space or a space with more dimensions. In the case of higher dimensionality, the dimensions greater than three can be composed of magnetocardiographic measurements, for example, or even of completely different physiologic measurements such as pulse oximetry, near-infrared spectroscopy, end-tidal CO2, EEG or other physiologic waveforms. FIG. 4 illustrates an example vector of the VCG 400 and its motion can be presented as projections of the vectorcardiograph onto one or more planes (e.g., the frontal 402, sagittal 404, and horizontal 406 planes).

As described in more detail below, a trajectory bifurcation can be identified based on comparison of a loop trajectory to previously stored control loop trajectories (e.g., a control loop generated based on an averaging of several prior loop trajectories). For example, a system can generate three orthogonal ECG vectors based on ECG data. By processing the orthogonal vectors, a loop trajectory can be determined and compared to a stored control loop trajectory. Differences in the loop trajectories can be used to identify trajectory bifurcation.

Figure 5:
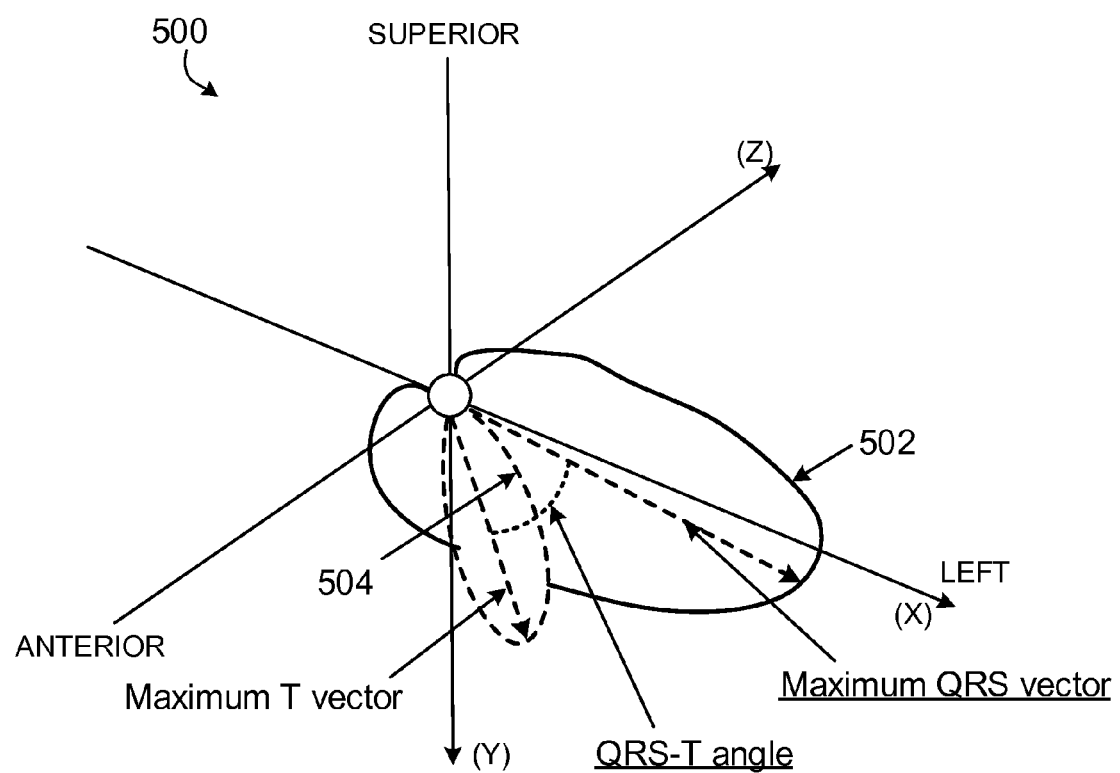
FIG. 5 is a graphical example of a VCG vector loop.

FIG. 5 shows an example path of the vector 500 in either three dimensional space, or as a projection onto a plane. At the beginning of each cardiac electrical cycle, just prior to the P-wave and QRS-wave, there is a period where the ECG is isoelectric. The isoelectric ECG marks the beginning of the VCG vector loop that begins and ends at the same isoelectric point and thus forms a loop. As can be seen in FIG. 5, the VCG can include multiple discrete loops corresponding to the QRS portion (e.g., loop 502) as well as the P-wave and T-wave portions (e.g., loop 504). The VCG portions can be treated as separate loops for the loop analysis and identification of a trajectory bifurcation. The trajectory bifurcation is defined as shift of the loop from one type of shape to another type of shape. The trajectory bifurcation can be a marker of elevated risk of impending acute degeneration of a patient's medical condition.

In one embodiment, standard 12 lead electrode placement and data acquisition and analysis hardware and software is used to generate a VCG vector loop. Exemplary 12 lead electrodes can be implemented in standard medical devices, such as X-Series monitors and defibrillators produced by ZOLL Medical®, Chelmsford Mass. The device can also take the form of a wearable defibrillator or monitor, such as the LifeVest produced by ZOLL Medical®, Chelmsford, Mass., which has two approximately orthogonal leads and thus can generate a two-dimensional vector loop. Techniques such as QRS detection, can be used to determine the start time fiducials for each ECG cycle. QRS rhythm morphologies can be classified to allow for removing intervals containing such beat classes as premature ventricular contractions (PVCs) from the analysis. It can be noted that the data and waveforms generated by single-lead, three-lead, five-lead and 12 lead ECGs, while they are vectors in the strict sense that they are a concatenated list of scalar values, cannot be considered as containing loops nor are they under the purview of vectorcardiography.

VCG loops can be generated for the overall segment as well as the P, T and QRS portions. In some embodiments, one or more groups of loop trajectories are collected for a duration of 10 seconds up to 30 minutes (e.g., 10 seconds up to 1 minute, 10 seconds up to 10 minutes, 10 seconds up to 20 minutes, 10 seconds up to 30 minutes). The groups of loop trajectories are of the segments (e.g., P, T, or QRS) or the overall cycle. Multiple groups of loops can be generated at different times. Each group is composed of one or more loops. The first group acts as a control group for comparison to a second group whose data was collected more recently than the control group (e.g., the second group of data is collected at a time subsequent to the collection of the first group of data). In order to make the comparison of the loops in the different groups, the shape of the loops in the control group are characterized. The characterization can be accomplished using a plurality of methods. For example, the characterization of the loop shape can be accomplished using statistical shape analysis.

In general, statistical shape analysis includes methods for studying the geometrical properties of random objects invariant under translation, scaling and rotation. The loop analysis described herein can be based on image analysis such as the statistical analysis using an Active Shape Model that includes global constraints with respect to shape. The global constraints can be determined from historical data (e.g., by machine learning) giving the model flexibility, robustness and specificity as the model synthesizes plausible instances with respect to the observations. In order to determine whether an object has changed shape, the shape of the object is first determined. In general, the shape refers to all geometrical information that remains when location, scale and rotational effects are filtered out from an object. Accordingly, the shape is invariant to Euclidean similarity transformations.

In addition to using the shape of an object in image analysis, other parameters used in the analysis can include a landmark, an anatomical landmark, mathematical landmarks, pseudo-landmarks, a configuration, a configuration matrix, and/or a configuration space, each of which is described briefly below. In general, a landmark refers to a point of correspondence on each object that matches between and within populations. Each landmark is associated with Cartesian coordinates, that is, either with an ordered pair of coordinates in the plane or with a triple of coordinates in 3D-space.

An anatomical landmark is a point assigned by an expert that corresponds between objects of study in a way meaningful in the context of the disciplinary context. In addition to the Cartesian coordinates, each landmark has a name denoting correspondence from shape object to shape object, for example, the point of the right elbow. Mathematical landmarks are points located on an object according to some mathematical or geometrical property of the figure. Pseudo-landmarks are constructed points on an object, either around the outline or in between anatomical or mathematical landmarks. The configuration is the set of landmarks on a particular object. The configuration matrix X is the $[k \cdot m]$ matrix of Cartesian coordinates of k landmarks in m dimensions. The configuration space is the space of all possible landmark coordinates. In applications we have landmarks in m=2 or m=3 dimensions.

Landmarks can also be referred to as homologous points, such as nodes, vertices, anchor points, fiducial markers, model points, markers or key points. Various methods for automatic landmark determination have been employed on the loops. For example, 10 points equidistant in time are selected and the amplitude at those points, or alternatively the maximum vector amplitude and the time at which that occurs is determined. Based in the identification of the maximum vector amplitude 5 points equidistant between the maximum point and the origin on each side of the maximum vector amplitude point are selected. In some implementations, the spacing can be different for each side of the maximum point due to the fact that the maximum vector amplitude point is not equidistant from the origin on each side.

In order to analyze the loop trajectories determined from the measured VCG, an alignment procedure can be used. An exemplary alignment procedure can include a Procrustes analysis. The alignment procedure can be performed in the shape space. The shape space is the set of all possible shapes of the selected object. More particularly, the shape space $\Sigma^n_k$ is the orbit shape of the non-coincident n point set configurations in the $IR^k$ under the action of the Euclidean similarity transformations. It can be important to understand the dimension spanned by this shape space. Given n random point vectors in k Euclidean dimensions the dimensionality is kn. The alignment procedure can reduce the number of dimensions (e.g., the data spans a subspace of kn). For example, the translation removes k dimensions, the uniform scaling removes one dimension and the rotation removes $\frac{1}{2}*k(k-1)$ dimensions. The shape space dimensionality can be defined as: $M=kn-k-1-k(k-1)/2$.

If a relationship between the distance in shape space and Euclidean distance in the original plane can be established, the set of shapes actually forms a Riemannian manifold containing the object class in question (e.g. hands), denoted as the Kendall shape space. The relationship between the distance in shape space and Euclidean distance in the original plane is called a shape metric. The shape metrics can include the Hausdorff distance, the strain energy, and the Procrustes distance. The Hausdorff distance and the strain energy compare shapes with unequal amount of points, the Procrustes distance requires corresponding point sets. Various shape metrics can be used in the methods described herein. Using the above-mentioned techniques of statistical shape analysis, the characteristics of the control group can be statistically parameterized.

In some embodiments, at subsequent time points (e.g., at 30 second or one minute intervals) a second, "test" group of trajectories can be collected, again, for durations of 10 seconds up to 30 minutes. The shape of the loops in the test group are characterized. The characteristics of the test group are then compared to the control group. The comparison techniques can include correlation matrices, Bookstein coordinates, centroid size, Procrustes analysis including planar, general or ordinary Procrustes analysis, the full Procrustes distance, Hotelling's T2 or Goodall's F-test to determine differences in the mean shape of loops for control and test groups and principal component analysis.

In some examples outline or contour analysis can be used additionally or alternatively to shape analysis to analyze the control and test groups of loops. In general, outline or contour analysis is based on digitizing a large number of points around the boundary of an object. For those situations in which landmarks are difficult to identify or obtain, if the outline can be represented by a closed curve or boundary, then outline analysis can substitute the shape analysis. Many shape objects that do not have clearly identifiable landmarks nevertheless can be analyzed successfully under such conditions. Use of outline analysis can be particularly useful in situations where paucity of landmarks is immediately apparent, although the representations of the loops can be easily differentiated visually.

In yet another example, Bayesian statistical shape analysis can also be employed when comparing the test to the control group. In some examples, a variation in landmark position can be used to identify differences between the control loops and test loops. One method for analysis of variation in landmark position is generally regarded as "Procrustes." This method includes a least-squares alignment of a set of landmark features to a mean shape, and this can be followed by eigenvector analysis of the linear correlations in variation around that mean. Methods as described in this paper or others on the subject can be used to compare the shape characterization for the first group, i.e. the control or baseline group of loops with the second, "test," loop or group of loops. Such measurements as principal component analysis, Procrustes distance, Hausdorff distance, or centroid size can be employed to compare the two groups.

Analysis of the baseline (e.g., control) group of loops with the second, "test," loop or group of loops can be used to determine a risk of impending acute degeneration of a patient's medical condition. The risk of impending acute degeneration of a patient's medical condition into cardiac arrest or other severe cardio-pulmonary conditions can be calculated by a variety of methods. In some examples, the risk can be calculated using a scoring model based on a mathematical model such as one based on logistic regression. Exemplary logistic regression models that can be used to calculate the risk include univariate analysis or multivariate non-linear regression.

In one embodiment, the logistic regression mathematical model can be used, for example, on data from samples of cardiovascular (CVS) and non-cardiovascular (non-CVS) patients. The logistic regression mathematical model can be fitted separately with a combination of demographic parameters (age), vital signs and other ECG parameters for the CVS and non-CVS patients. The prediction performance can be investigated through Receiver Operating Characteristic (ROC) analysis as well as Sensitivity, Specificity, Positive Predictive Value (PPV) and Negative Predictive Value (NPV). Based on the logistic model, a risk score that can be a score from 0-100% is generated at regular intervals, typically on the order of every 10 seconds. In other examples, the risk score can be generated at regular intervals such as 30 seconds, 1 minute, or 5 minutes. The logistic model can take into account the first, second and higher order derivatives of the shape distance between the first and second groups of loops. In other words, if the distance is diverging more rapidly, that is a sign of the patient's condition degenerating more rapidly and this in itself will elevate the risk score. In some examples, the intervals at which the risk score is calculated is a function of the perceived risk. For example, the frequency of the calculation can be increased upon identification of an increased risk level (e.g., upon a determination that a risk level exceeds a threshold risk level).

Separate risk scores can be calculated for different time periods, for instance, separate risk score for risk of an event before 10 minutes, 1 hour, 2 hours, 4 hours, 8 hours, 12 hours, 24 hours, 48 hours, and 72 hours. The patient monitoring device can display the risk scores as a list, can display one or more from the list based on user input selection from the user, or can show the risk displayed as a curve on the display. As such, a time-dependent risk calculation and evolution can be generated and displayed to the patient or medical professional.

Figure 6:
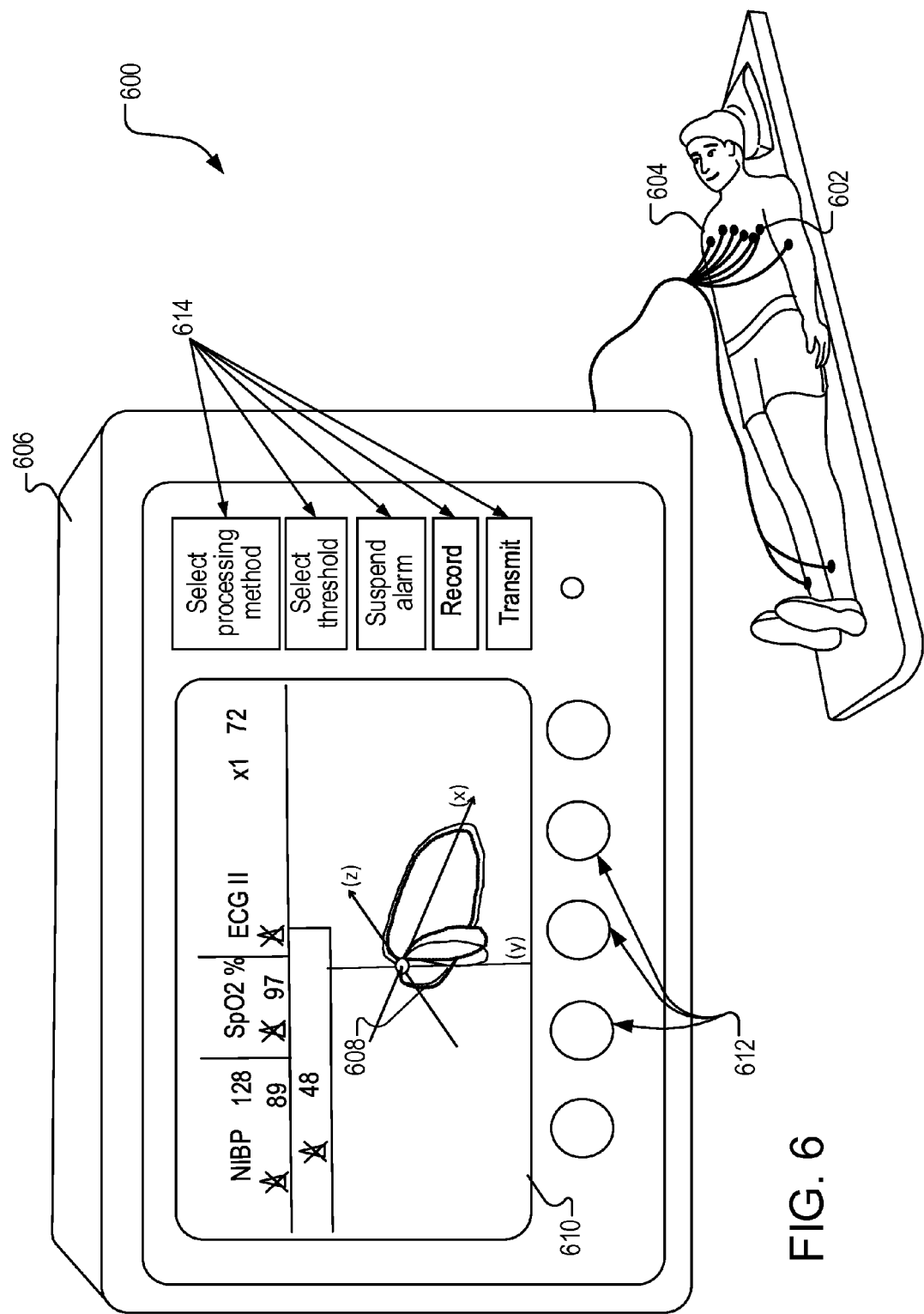
FIG. 6 is a schematic illustration of an example patient monitoring system.

FIG. 6 illustrates an example patient monitoring configuration 600. The example, patient monitoring configuration 600 includes three or more electrodes 602, attached to various locations on the body surface of the patient 604. In this example, a 62 lead ECG with 62 electrodes is shown. The electrodes 602 are electrically coupled to the patient monitoring device 606. An example of a patient monitoring device 606 can be a standard ECG monitoring device, a portable ECG monitoring device, a defibrillator, a smartphone, a personal digital assistant (PDA), a laptop, a tablet personal computer (PC), a desktop PC, a set-top box, an interactive television and/or combinations thereof or any other type of medical device capable to record and process ECG signals.

In the pictured example, the patient monitoring device 606 is configured to acquire and display a VCG signal 608 via the electrode package 602. This VCG signal can be used in the identification of trajectory bifurcation based on an analysis of a loop or group of loop trajectories (e.g., represented as solid lines) compared to a control group of loops (e.g., represented as dashed lines) as described herein. The monitoring device 606 also enables user input via the user interface 610 and additional control buttons 612 and 614. In some implementations, the control buttons 612 can enable a user to select one of a plurality of available graphical user interfaces 610, described in detail with reference to FIGS. 7-9. Graphical user interfaces 610 provide a medical professional with various representations of the VCG signal and other information that can aid in developing a treatment plan for the patient 604. In some implementations, the control buttons 614 can enable a user to initiate, stop or modify particular actions that can be performed by the patient monitoring device 606. Actions that can be initiated, stopped or modified by using the buttons 614 can include the selection of processing method, selection of an alarm threshold, suspension of alarm, recording of data and transmitting data over the network to a remote device.

Figure 7:
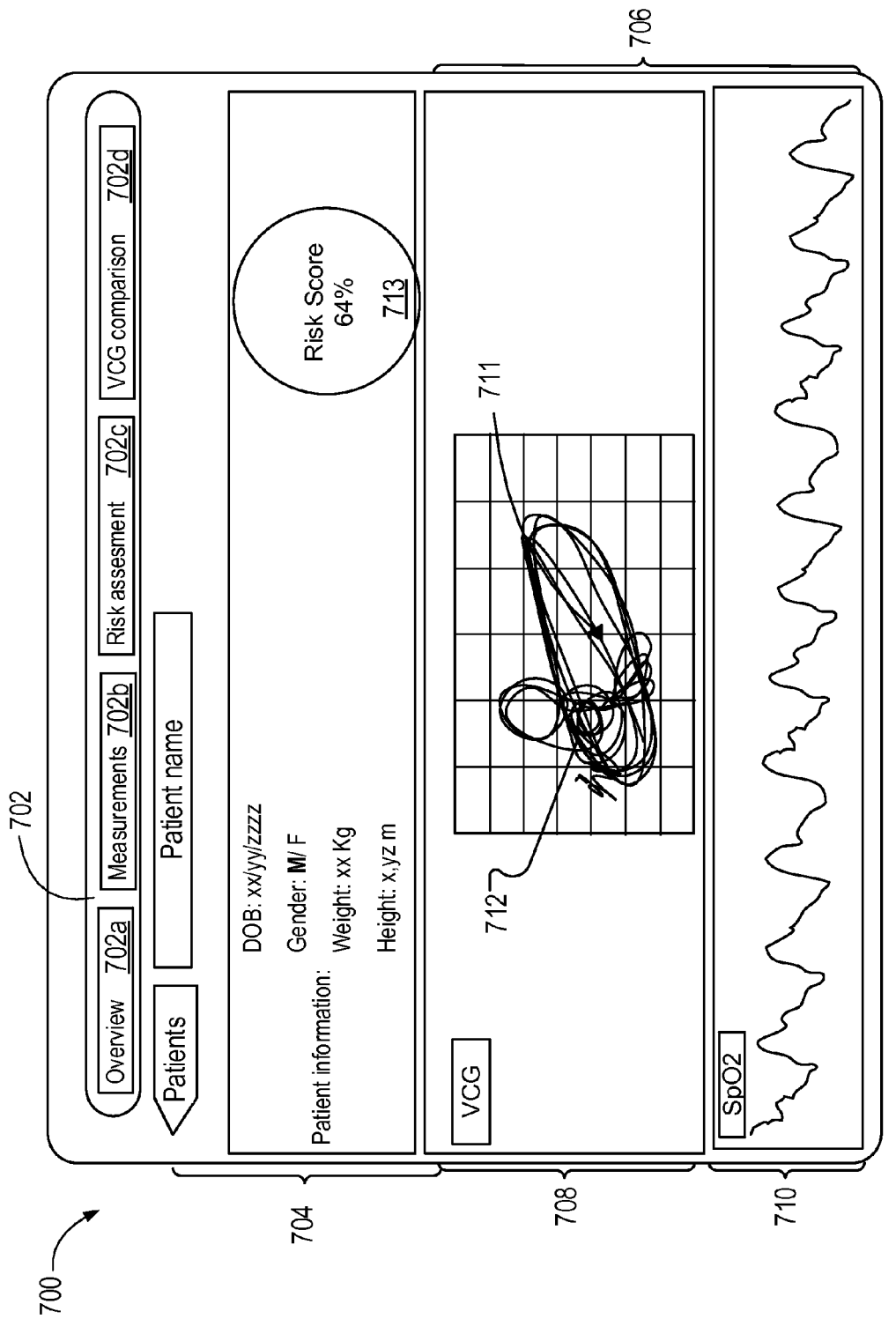
FIG. 7 is an example of a graphical user interface displaying patient data, including a trajectory bifurcation.

FIG. 7 illustrates an example graphical user interface (GUI) 700 to graphically represent patient data on the display of a device associated with the patient monitoring device 606 (FIG. 6), such as a computer or a remote display device. The example patient data discussed herein corresponds to real-time or recorded VCG data. In particular, GUI 700 provides cardiac information relating to data collected from electrocardiogram monitors coupled to the patient.

In some implementations, GUI 700 enables a user to select a patient (e.g., a medical professional might be able to access information about multiple patients under their care). For each selected patient, GUI 700 can display patient statistics, recorded data, determined data and other medical information related to the patient. The determined data that can be displayed by GUI 700 includes the VCG 712 and parameters derived from VCG, such as the trajectory bifurcation and a risk indicator 713 (as described in more detail below).

The example illustrated in FIG. 7 displays both patient statistics and recorded data. A particular display of patient information can be selected by a user interacting with the header 702, which includes multiple tabs. In some implementations, the header 702 includes an overview tab 702*a*, a measurements tab 702*b*, a risk assessment tab 702*c* and a VCG comparison tab 702*d*. In some implementations, a user of the patient monitoring device can personalize the header 702, by adding or deleting a number of tabs. For example, the user can add a tab for patient history.

GUI 700 corresponds to an overview tab. The GUI 700 includes a patient statistics area 704 and a patient data area 706. Patient statistics area 704 includes information such as a name, gender, weight, height, and age of the particular patient, to which the displayed patient data corresponds. The patient statistics area 704 can also include the current date and time, and other information (e.g., heart rate, PR interval, QT interval, QRS duration). The patient statistics area 704 can also include an indicator 713 associated with the calculated risk score. For example, the risk score can be displayed as a numeric value and can also be color-coded, for instance it can turn from green to red if the risk score exceeds a threshold value of, for example, 70%.

Patient data area 706 includes a first display portion 708, and a second display portion 710. The first display portion 708 and the second display portion 710 each provide patient data as full traces of patient data for a particular period of time, graphically representing the data collected over the particular period of time. As illustrated in FIG. 7, the first display portion 708 can display a VCG 712 corresponding to multiple cardiac cycles. In some implementations, the real time motion of cardiac vectors in 3D space can be indicated by a marker 711. The marker 711 can be a geometrical shape (e.g., shown here as a triangle). In other examples, the VCG 712 corresponds to multiple cardiac cycles and the display can highlight the display of the current cycle. For example the highlighting of a physiological waveform can involve using thicker lines of darker colors.

The second display portion 710 can include additional patient data. For example, the signal displayed in the second display portion 710 can be blood oxygen saturation (SpO2), as displayed in FIG. 7, blood pressure, or any other signal that can be recorded and displayed by the patient monitoring device. The risk score can also be represented as a waveform along with SpO2 or other physiologic waveforms. In some implementations, a user can modify the data displayed within patient data area 706. The data can be modified by a user clicking on the title of a display portion 708 or 710 enabling a selection from an available drop down list.

Figure 8:
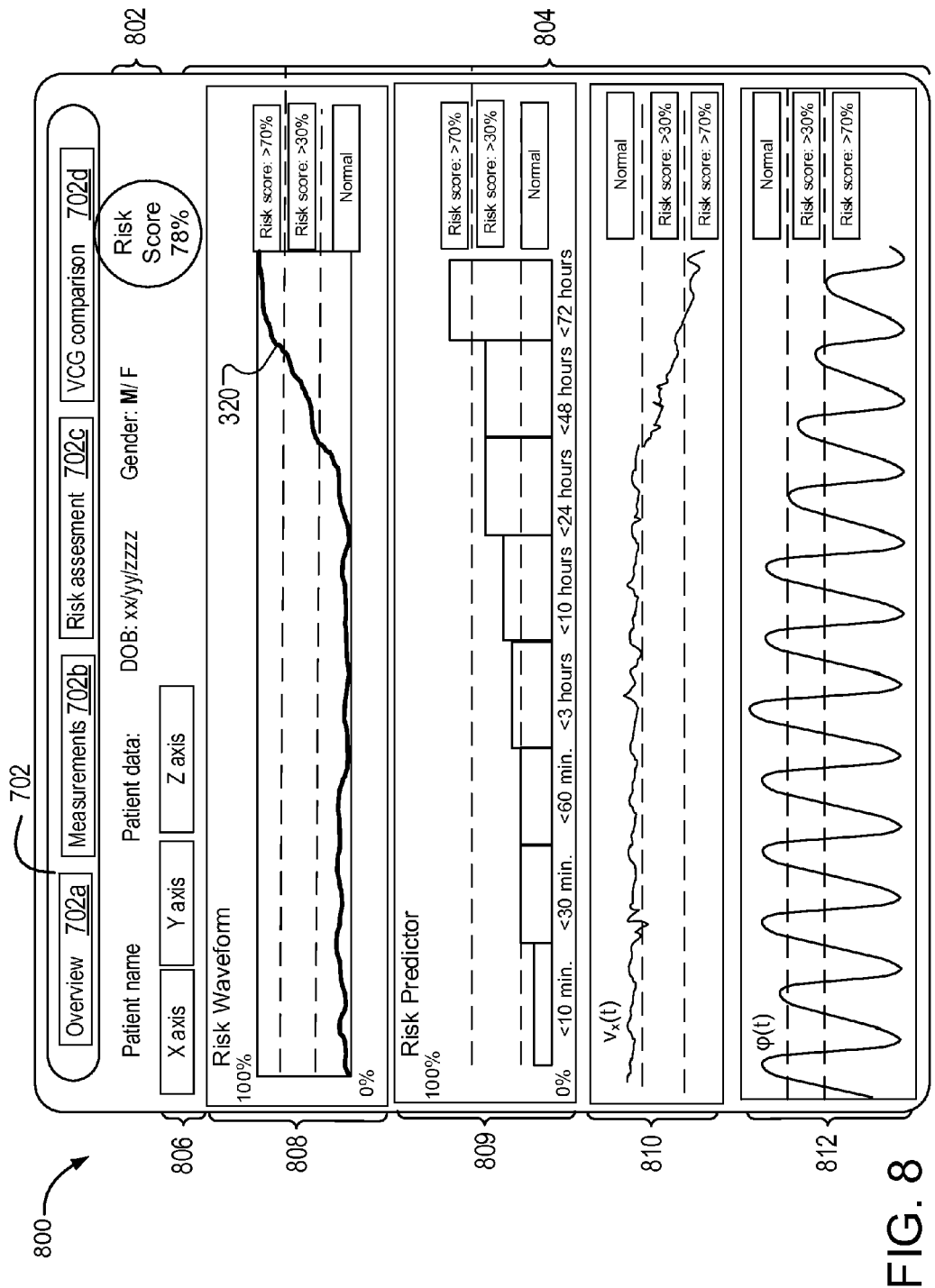
FIG. 8 is an example of a graphical user interface including a risk waveform.

Referring to FIG. 8, an example GUI 800, corresponding to a selected risk assessment tab 702c, is illustrated. The GUI 800 includes a patient statistics area 802 and a patient data area 804. The patient statistics area 802 can include information similar to the patient statistics area 704 shown in FIG. 7. The patient data area 804 can include various information to enable a caregiver to assess risk of an impending acute event. The patient data area 804 includes various portions 808, 809, 810, 812, displaying different information.

The first display portion 808 can illustrate the calculated risk score waveform 820. In general the risk score waveform 820 shows a percentage risk (e.g., scaled from 0 to 100% risk) as a function of time. Curve 820 provides a historical view of the calculated risk over a period of time. This enables a caregiver to view whether the patient's risk level is increasing or decreasing and modify treatment accordingly.

The second display portion 809 can illustrate the predicted risk for a patient. For example, a risk score can be calculated for various periods of time in the future (e.g., risk of an event within 10 minutes, 80 minutes, 1 hour, 8 hours, 10 hours, 24 hours, 48 hours, 72 hours). This information can be displayed graphically to allow a caregiver to assess both the current risk and future risk of an event.

In general, as shown in FIG. 7, the VCGs are displayed as loops. Other displayed components can include, but are not limited to, loop centroid area, loop angle, loop width. The third display portion 810 can display the speed of the VCG within the T wave loop. The speed can be defined as: $vx(t)=\Delta v/\Delta t$, where $\Delta v=\|=v(t)-v(t+\Delta t)\|$ and $vx(t)$ represents the projection of the speed on the x axis, as function of time. The fourth display portion 812 can display one of the phase angles of the VCG, which can be determined can be based on the following equation: $\cos \phi(t)=v_x(t)/\sqrt{v_x^2+v_y^2+v_z^2}$. In some additional examples, conventional ECG waveform can be shown on the display with a box containing the VCG loop that overlays or is just slightly above or below the ECG trace. The box can then be slid along the ECG trace with the displayed loop in the box corresponding to the ECG cycle underneath the box on the display.

Figure 9:
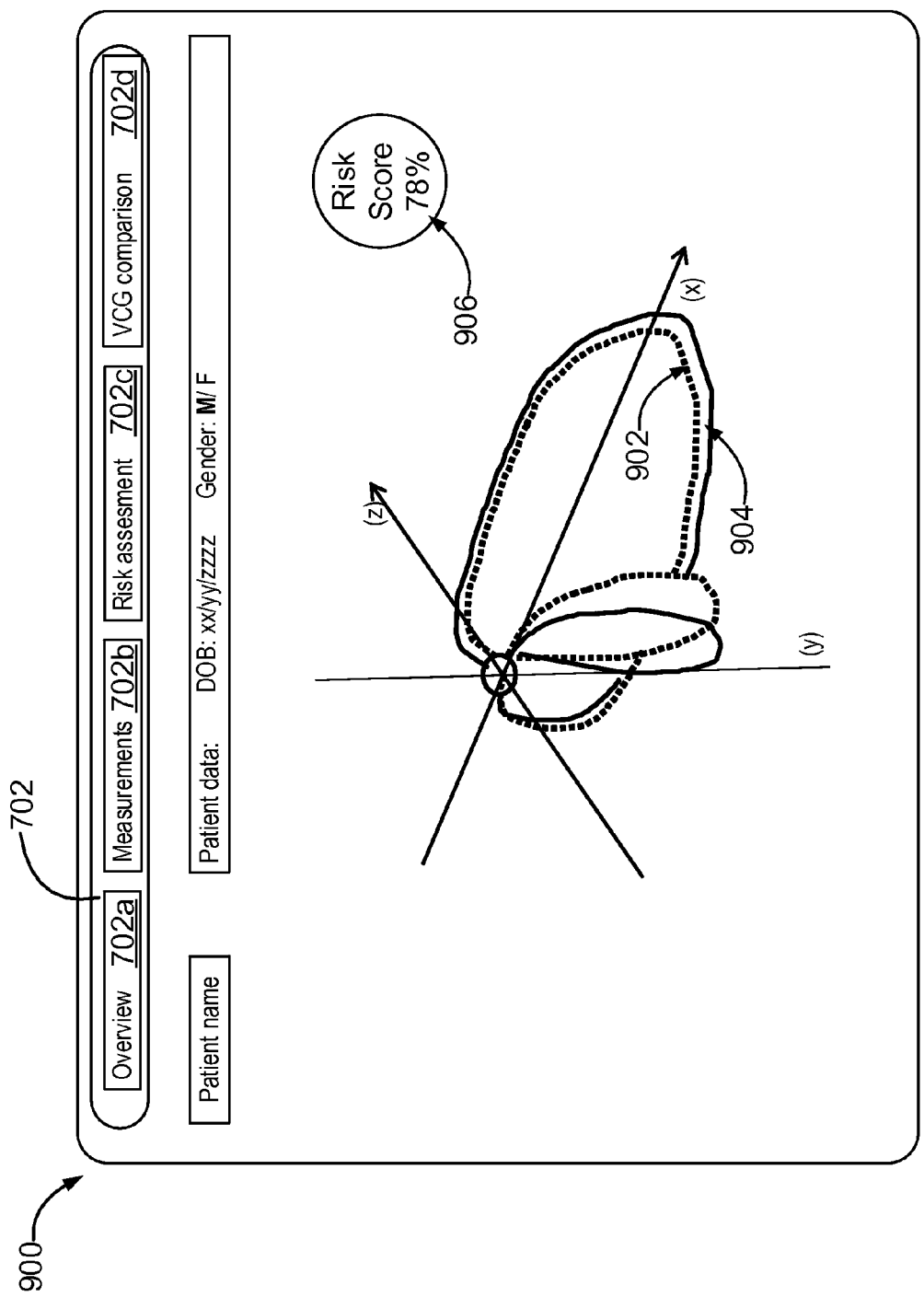
FIG. 9 is an example of a graphical user interface including a control loop and a test loop.

Referring to FIG. 9, an example GUI 900, corresponding to a selected VCG comparison tab 702d, is illustrated. The display 900 can include a visual identifier to provide an indication of trajectory bifurcation identified based on the processed VCG signals. For example GUI 900 displays both a test loop 902 and a control loop 904 to allow visual comparison by a caregiver. More particularly, the mean shape of the first group control loop trajectory can be displayed as a dashed line or marked by a visual indicator (e.g., represented by line 902), to enable differentiation from the representation of the second "control" group of loop trajectories (e.g., represented by line 904). In some examples, the difference between the two loop representations—the control and test groups—can be shown as a color-coded area on the display that indicates visually the differences between the loops. An indicator 906 of the risk score calculated based at least in part on the differences between the two loops can also be provided on display 900.

Figure 10:
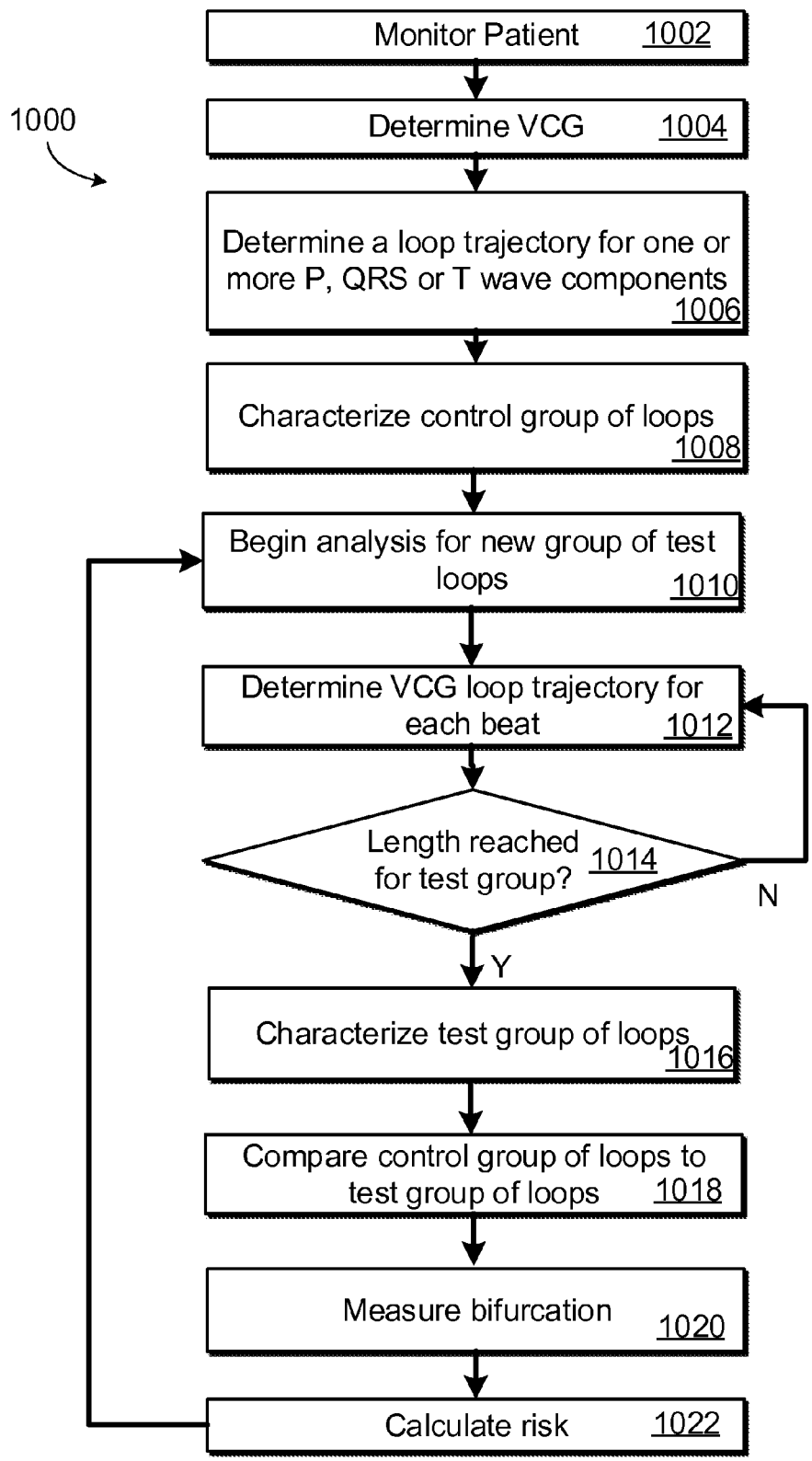
FIG. 10 is a flow chart of a process for identifying trajectory bifurcation and calculating a risk score.

Referring to FIG. 10, an example method 1000 is shown for determining a cardiac risk indicator based on identification of T wave bifurcations. In one embodiment, the method 1000 is implemented by the example patient monitoring device described herein. However, other embodiments are possible.

At a step 1002, a patient is monitored, by recording one or more types of physiological data, including an ECG signal. The ECG signal can be received from any appropriate source of patient ECG data. For example, ECG data can be received in real-time from three or more ECG electrodes attached to a patient or previously recorded data can be received from a storage device. ECG data can be of any appropriate type. ECG data can be recorded from a plurality of lead sites on the surface of the patient's body. In some implementations, standard 12-lead ECG recordings (e.g., leads I, II, III, aVR, aVF, aVL, V1, V2, V3, V4, V5 and V6) can be derived based on signals retrieved with 10 ECG electrodes. Any appropriate number of ECG electrodes, attached to appropriate body sites, can be used. Examples of other ECG lead systems include the "Frank" electrode lead system (e.g., 6 electrodes), the McFee-Parungao Lead System, the SVEC III Lead System, Fischmann Barber-Weiss Lead System, and the Nelson Lead System. Other examples include addition of right-sided precordial leads, posterior leads, leads placed in higher or lower intercostal spaces, and the like.

In some implementations, information about the source of the ECG data can be provided to the patient monitoring device 606 (see FIG. 6). For example, the patient monitoring device can adapt the configuration of the display and/or analysis tools based on the source of the ECG data, such as the position of the ECG leads with respect to the heart, the body, and/or to other leads. In some implementations, the patient monitoring device can perform real time ECG signal pre-processing. Real time ECG signal pre-processing can include removing the DC component with a high-pass filter, amplifying the ECG signal, limiting the signal bandwidth with a low-pass filter and digitally sampling the ECG signal. In some implementations, the ECG signal is received together with additional patient data, including patient statistics, other physiological data recordings, medical history, physical exam findings and other medical information that might be requested by a user. Patient data can be used in conjunction with patient-specific ECG data for data processing and display, or it can be used to correlate information extracted from the ECG data.

At step 1004, a VCG signal is determined based on the received ECG signal. ECG data provides a time-dependent voltage that describes the electrical activity of the heart, which is treated like a dipole having an origin at the center of the patient's heart. Multiple ECG lead sites provide different time-dependent voltage waveforms that reflect the overall cardiac electrical activity. A time-dependent heart vector that represents the size and orientation of the time-varying electrical dipole can be calculated by approximating the electrical activity of the heart.

Additionally, at step 1004, three or more ECG leads can be used to generate the vectorcardiograph, typically using the X, Y, Z orthogonal components for the representation of the VCG vector. A conversion matrix can be used to convert a particular set of leads to the $V_x$, $V_y$, $V_z$ orthogonal components of the VCG vector. In some implementations, a VCG heart vector can be derived from the ECG using an inverse transform (e.g., an inverse Dower matrix, Levkov matrix). Any conversion method can be used to generate the VCG heart vector based on the ECG data.

At a step 1006, the process determines a loop trajectory including a portion of ECG cycle. The portion of ECG cycle can be a P, QRS or T wave. Determining a portion of the ECG cycle can include detecting an onset of the portion of the ECG cycle and an end of the portion of the ECG cycle, isolating the portion of the ECG cycle based on detecting the onset of the portion of the ECG cycle and the end of the portion of the ECG cycle and filtering the isolated portion of the ECG cycle. The portion of ECG cycle can be determined for each cardiac cycle of the received ECG.

In some implementations, the information about the plurality of cardiac cycles is used to calculate a characterization of a plurality of cardiac cycles to generate the control loop trajectory; and store the control loop trajectory. In some implementations, the characterization can include a spline estimation of the loop trajectories corresponding to a plurality of cardiac cycles. As mentioned previously, statistical shape analysis can be used to characterize the loop or groups of loops. For example, a control group of loop trajectories can be generated automatically at the beginning of the monitoring session. There can be a user input on the patient monitoring device to allow the user to manually initiate a new acquisition of the control group of loop trajectories. The control group can be composed of two or more ECG cycles. In some implementations, the control group of loop trajectories corresponds to 30 seconds up to 72 hours of ECG data. The time period can be configured in the non-volatile storage memory of the patient monitoring device.

At step 1008, the system characterizes the control group of loops. An analysis, such as a statistical one, is performed on the loop trajectories for the different cardiac cycles. As such, the shape of the control loop represents a statistical representation, oftentimes in the form of a mean, of the shapes of observed loop trajectories during the control window.

In another example, the odd beats or even beats are used to generate the control or test loop trajectories. In this way, the analysis can analyze for the effects of T-wave alternans. Thus, the control group can be every odd element in a time period, and the test group can be every even element in the same time period, or vice versa. This will provide a more accurate measure of T-wave alternans. In more elaborate implementations, the shape characteristics of the control and/or test groups can be determined using every kth loop, $L_k$, of the group under analysis. For instance, for k equal to 3, the control group would be composed of the 1st, 3rd, 6th, 9th, etc., of the original group under analysis. The test group can then be composed of the 2nd, 5th, 8th, etc. following the end of the control group acquisition period.

In a further elaboration, for any particular value of k, multiple subgroups of the control period interval can be created, for instance, for k=4, you can start at loop 1, 2, 3 or 4, to create 4 distinct groups of loops for characterization of the shape using such methods as statistical shape analysis. A single group from within these subgroups can be chosen as the control group by analyzing the statistical variance of the shape of the subgroups and choosing the subgroup that is the most self-consistent with the lowest variation in shape. Thus, for each interval up to about 8 or 10, or whatever is computationally practically given the state of the art with microprocessors, a control group is created for each value of k, and at regular intervals, even as rapidly as every new loop, the test group can also be decomposed into the k subgroups and compared to the control subgroups for degree of trajectory bifurcation.

In some implementations, the characterization can be based on an average or median of loop trajectories corresponding to the plurality of cardiac cycles. In some implementations, the test group of loop trajectories corresponds ECG data recorded within last 5 seconds up to 60 minutes from present time. The time period corresponding to the test group of loop trajectories can be separated by at least 5 minutes from the time period corresponding to the control group. At steps 1010-1016 the test group of loop trajectories is generated. At step 1010 the analysis for a new group of test loops begins. This analysis of a new group of test loops can be based on a time threshold (e.g., a new set of loops is analyzed every 10 minutes or every 30 minutes) or can be based on a physiological trigger such as an increased risk score or another factor indicative of a change in the status of the patient. At step 1012, a VCG loop trajectory is determined for a particular beat that will be included in the set of test loops. For example, two or more ECG leads can be used to generate the vectorcardiograph, typically using the X, Y, Z orthogonal components for the representation of the VCG vector. The system determines (e.g., at step 1014) if the length for the test group has been reached. For example, the size of the test group can be based on a threshold number of loops and/or on a time based threshold. If the length has not been reached, the system continues to determine loop trajectories to add to the test group. If the length has been reached, at step 1016, the system characterizes the test group of loops.

The loop trajectories determined at steps 1006 (control loops) and 1012 (test loops) can be at least three dimensional. For example, a first dimension can include a first spatial component of the loop trajectory, a second dimension can include a second spatial component of the loop trajectory orthogonal to the first dimension and a third dimension can include a third spatial component of the loop trajectory orthogonal to the first dimension and the second dimension. In some implementations, the loop trajectory can include more than three dimensions. For example, a fourth dimension can include an additional physiological signal co-registered with the ECG signal.

At step 1018, the system compares the control group of loops to the test group of loops. At step 1020, the trajectory bifurcation is identified by comparing the test loop trajectory to a control loop trajectory. In some implementations, the trajectory bifurcation can be identified based on a statistical analysis. For example, a variation of the loop trajectory from the control loop trajectory that occurs for a portion of the ECG signal and exceeds the standard deviation of the control loop trajectory can be identified as a trajectory bifurcation. As another example, the statistical analysis used for the identification of the trajectory bifurcation can be a non-Gaussian statistical analysis.

In some implementations, the action of trajectory bifurcation identification can include calculating an area of the loop trajectory and subtracting the area of the loop trajectory from an area of the control loop trajectory. In some implementations, the identification of the trajectory bifurcation leads to an automatic generation of a bifurcation.

In some implementations, the step 1020 is repeated at least three times to compare the trajectory bifurcation of at least three consecutive cardiac cycles of the plurality of cardiac cycles to determine a trend of the trajectory bifurcation and based on the trend, to define an episodic trajectory bifurcation. The action of identifying the trajectory bifurcation can be repeated cyclically over multiple cardiac cycles. For example, the trajectory bifurcation can be identified for each recorded cardiac cycle, after the control loop trajectory was determined.

At step 1022, an indicator is generated based on the identification of the trajectory bifurcation. In some implementations, the indicator can include a cardiac risk score (e.g., a quantitative risk estimated value) based on the identification of the trajectory bifurcation and an alarm that alerts a user of the remote device In some implementations, a user of the remote device can select a treatment plan based on the indicator that can be delivered to the monitored patient.

Figure 11:
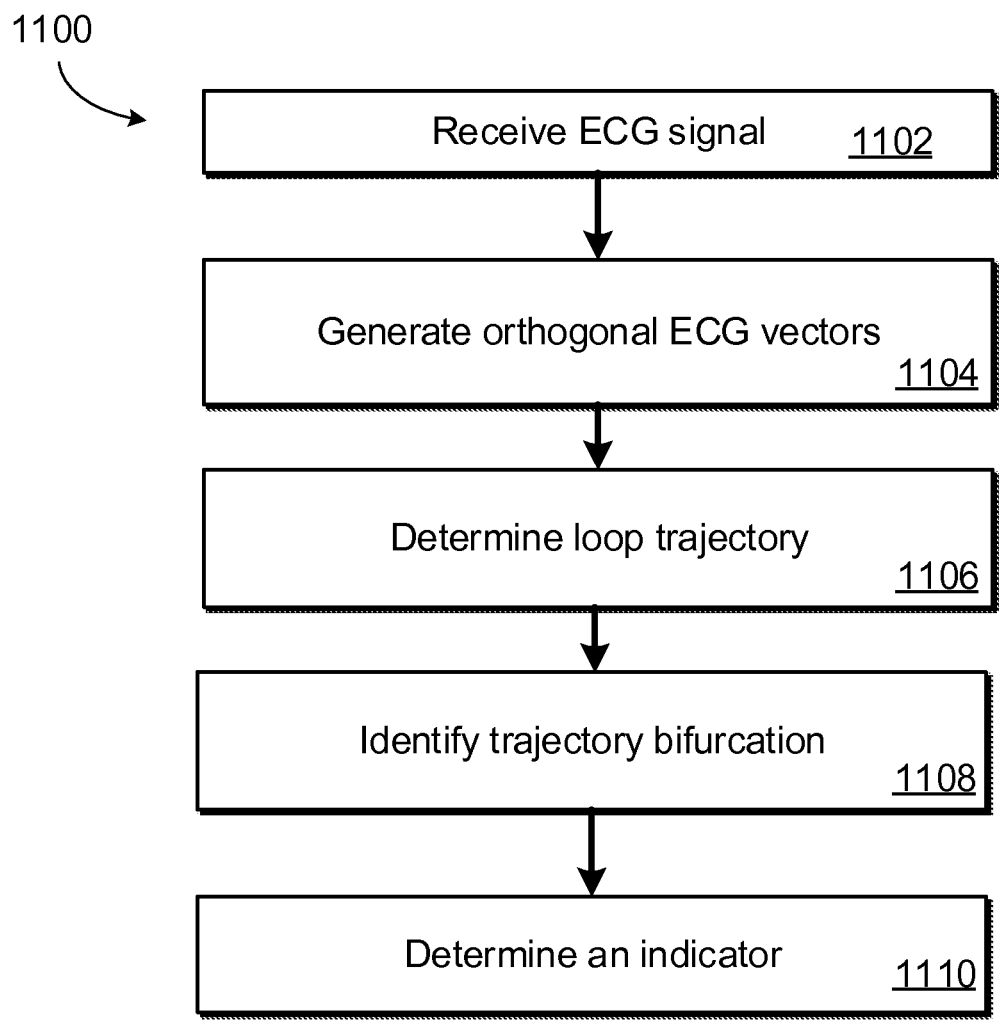
FIG. 11 is a flow chart of an example process for identifying a trajectory bifurcation.

Referring to FIG. 11, an example method 1100 is shown for determining an indicator of a cardiac event. In one embodiment, the method 1100 is implemented by the example patient monitoring device described herein. The patient monitoring device can be a defibrillator, a pacemaker, a computing device or another type of device.

At a step 1102, an ECG signal can be received from any appropriate source of patient ECG data including two or more ECG leads. In some implementations, the ECG signal is received together with additional patient data.

At step 1104, a VCG signal is generated based on the received ECG signal. Any conversion method can be used to generate the VCG heart vector based on the ECG data. At a step 1106, the process determines a loop trajectory including a portion of ECG signal. The portion of ECG signal can be a T, QRS or P wave. Determining a portion of the ECG signal can include detecting an onset of the portion of the ECG signal and an end of the portion of the ECG signal, isolating the portion of the ECG signal based on detecting the onset of the portion of the ECG signal and the end of the portion of the ECG signal and filtering the isolated portion of the ECG signal. The portion of ECG signal can be determined for each cardiac cycle of the received ECG.

At step 1108, a trajectory bifurcation is identified by comparing multiple loop trajectories (e.g., a test loop trajectory to a control loop trajectory) for a plurality of cardiac cycles. In some implementations, the trajectory bifurcation can be identified based on a statistical analysis. In some implementations, the step 1108 is repeated multiple times to compare the trajectory bifurcation of multiple consecutive cardiac cycles, to determine a trend of the trajectory bifurcation and, based on the trend, to define an episodic trajectory bifurcation.

At step 1112, an indicator of a cardiac event is determined based on the trajectory bifurcation. In some implementations, the indicator can include a cardiac risk score (e.g., a quantitative risk estimated value) based on the identification of the trajectory bifurcation and an alarm that alerts a user of the remote device In some implementations, a user of the remote device can select a treatment plan based on the indicator that can be delivered to the monitored patient.

Figure 12:
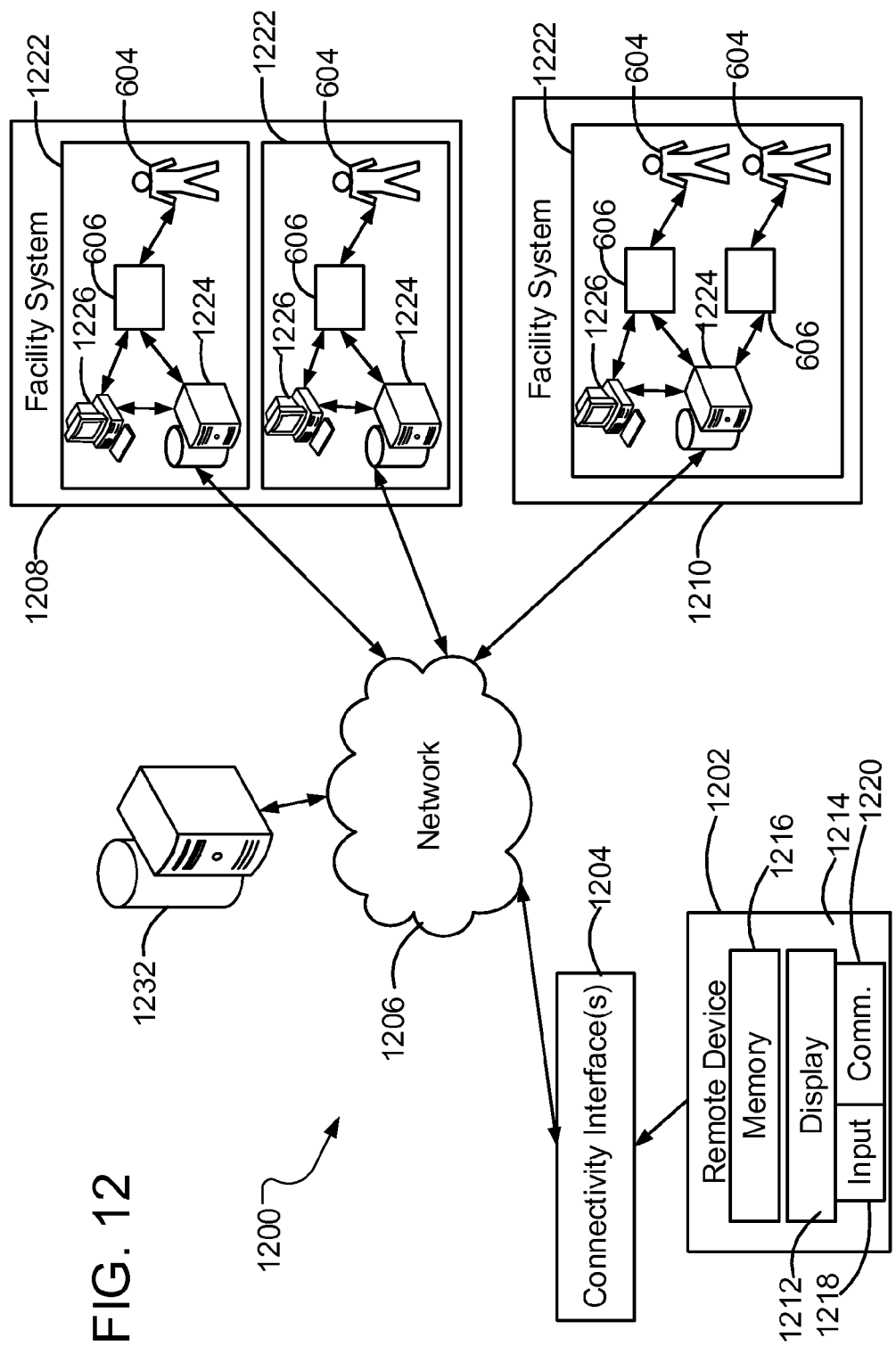
FIG. 12 is a schematic illustration of an example system.

Referring to FIG. 12, an example system 1200 for monitoring and processing patients VCG is illustrated. For example, a caregiver can view information about multiple patients via a remote device 1202. This enables the caregiver to identify patients with increased risk and deploy the appropriate personnel to attend to the situation and determine appropriate treatment. System 1200 includes a remote device 1202, connectivity interface(s) 1204, a network 1206, a first facility system 1208, and a second facility system 1210. As discussed in further detail herein, data is transferred from each of the first and second facility systems 1208 and 1210 through the network 1206 and connectivity interface(s) 1204 for presentation, or display on the remote device 1202. Further, data can be transferred from the remote device 1202 through the connectivity interface(s) 1204 and network 1206 to each of the first and second facility systems 1208 and 1210, respectively. For example, data associated with a treatment plan for correcting a trajectory bifurcation identified in a VCG of a patient 1209 can be transferred between the remote device 1202 and the corresponding facility system 1208 or 1210. Although a single remote device 1202 is illustrated, it is contemplated that one or more remote devices 1202 can communicate with each of the first and second facility systems 1208, 1210 through the network 1206 and connectivity interface(s) 1204. Similarly, although two facility systems are illustrated, the present disclosure can be implemented with one or more facility systems.

Implementations of the present disclosure are discussed in further detail herein with reference to an example context. The example context includes a patient monitoring processes and in particular identification of cardiac abnormalities. Within the context example, the cardiac activity of a patient can be continuously monitored by the patient monitoring device 606, which includes an ECG recording device. The patient monitoring device 606 can include the patient information system 1224 and the computer interface 620, forming a part of or a complete system for indicating cardiac risk.

The system for indicating cardiac risk can provide status changes that can occur automatically upon the identification of an event (e.g., trajectory bifurcation). Executability of the actions and identification of the events are constrained or guided by strict processing rules, which can vary for different facility systems 1208 and 1210. For example, in some cases, patient data is transferred to a remote device 1202 at the identification of an event (e.g., trajectory bifurcation). In other cases, data can be transferred upon a request of a user of the remote device 1202.

The remote device 1202 can include any number of devices. Such devices include, but are not limited to, a mobile phone, a smartphone, a personal digital assistant (PDA), a laptop, a tablet personal computer (PC), a desktop PC, a set-top box, an interactive television and/or combinations thereof. The remote device 1202 includes a display 1212, a processor 1214, memory 1216, an input interface 1218, and a communication interface 1220.

The remote device 1202 can communicate wirelessly through the communication interface(s) 1204, which can include digital signal processing circuitry. The communication interface(s) 1204 can provide communications under various modes or protocols including, but not limited to, GSM voice calls, SMS, EMS or MMS messaging, CDMA, TDMA, PDC, WCDMA, CDMA2000, and/or GPRS. Such communication can occur, for example, through a radio-frequency transceiver (not shown). Further, the remote device can be capable of short-range communication using features including, but not limited to, Bluetooth and/or WiFi transceivers (not shown).

The remote device 1202 communicates with the network 1206 through the connectivity interface(s) 1204. The connectivity interface(s) 1204 can include, but is not limited to, a satellite receiver, cellular network, a Bluetooth system, a Wi-Fi system (e.g., 1202.x), a cable modem, a DSL/dial-up interface, and/or a private branch exchange (PBX) system. Each of these connectivity interfaces 1204 enables data to be transmitted to/from the network 1206. The network 1206 can be provided as a local area network (LAN), a wide area network (WAN), a wireless LAN (WLAN), a metropolitan area network (MAN), a personal area network (PAN), the Internet, and/or combinations thereof.

In the systems of FIG. 12, the first facility system 1208 includes a plurality of facilities 1222, and the second facility system 1210 includes a single facility 1222. Each facility 1208, 1210 or 1222 includes an associated patient information system 1224, computer interface(s) 120, and patient monitoring device(s) 1208. In some implementations, the patient information system 1224 can include a cardiology information system. Although the system architecture 1200 includes a patient information system 1224 located at each facility 1222, it is contemplated that the facilities 1222 can communicate with a common patient information system 1224 that is remotely located from either facility 1222, or that is located at one of the facilities 1222 within the facility system 1208, 1210.

Each patient monitoring device 606 is configured to monitor physiological characteristics of a particular patient 1209, to generate data signals based thereon. In the example context of the present disclosure, the patient monitoring devices 1208 include ECG recording devices and one or more processors. The data signals are communicated to the patient information system 1224 which can collect patient data based thereon, and store the data to a patient profile that is associated with the particular patient. The patient monitoring device 606 can communicate with the patient information system 1224 and/or the computer interface 620 via a direct connection, or remotely through a network (not shown) that can include, but is not limited to, a LAN, a WAN, a WLAN, and/or the Internet.

In some cases, the patient data can include the recorded ECG, data extracted from the processed ECG (e.g., VCG, portion of ECG, trajectory bifurcation and indicator) and, optionally, additional physiological data coregistered with the ECG. The patient data can be made available for display on remote device 1202 and/or directly at the patient monitoring device 1208. A healthcare provider (e.g., a technician, a nurse and/or physician) can augment the patient data by inputting patient information that can be stored to a patient information system 1224. More specifically, the healthcare provider can input patient information corresponding to a particular patient 1209, which patient information can be stored to the patient profile.

As discussed above, each patient information system 1224 stores patient data that can be collected from the patient monitoring devices 1208, as well as additional patient information, that can include information that is input by a healthcare provider. The patient information system 1224 communicates the patient data and/or the additional patient data to a data management system (DMS) 1232. The DMS 1232 can be provided as a server, or a virtual server, that runs server software components, and can include data storage including, but not limited to, a database and/or flat files. In the example system architecture of FIG. 12, a common DMS 1232 is provided. The DMS 1232 can be common to various facility systems 1208, 1210, without being associated with a particular facility system 1208, 1210. Each patient information system 1224 communicates with the DMS 1232 via a direct connection, or remotely through a network (not shown) that can include, but is not limited to, a LAN, a WAN, a WLAN, and/or the Internet. The DMS 1232 can communicate ancillary information (e.g., treatment plan) to the patient information system 1224. In some implementations, each facility system 1208, 1210 can include a corresponding DMS 1232. In such an arrangement, each patient information system 1224 communicates patient data, and/or additional patient data to the DMS 1232.

The example system architecture of FIG. 12, provides for the remote location of data collection at the DMS 1232. In such implementations, the DMS 1232 can be provided at a third-party site, remote from any of the facilities 1222, or facility systems 1208, 1210.

The DMS 1232 synchronizes and transfers data between the remote device 1202, or multiple remote devices 1202, and multiple patient information systems 1224. More specifically, the DMS 1232 processes and prepares the patient data and/or patient information for transfer to and presentation on the remote device 1202 from the patient information system 1224. The DMS 1232 also processes and prepares ancillary information for transfer to and storage in the patient information system 1224 from the remote device 1202, or for potential presentation at a corresponding computer interface 620.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having an LCD (liquid crystal display) or LED display for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a frontend component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

Many other implementations other than those described may be employed, and may be encompassed by the following claims.

What is claimed is:

1. A system, comprising:
   three or more ECG leads configured to receive an ECG signal; and
   a first computing device comprising a processor coupled to a memory, the processor and the memory configured to perform operations comprising:
      generating at least two orthogonal ECG vectors based on the ECG signal of a patient,
      processing the at least two orthogonal ECG vectors to determine a loop trajectory of at least a portion of the ECG signal,
      identifying a trajectory bifurcation by comparing the loop trajectory to a control loop trajectory for at least three consecutive cardiac cycles of a plurality of cardiac cycles,
      determining a variation of the trajectory bifurcation over time, the determination based on an analysis of the trajectory bifurcation of the at least three consecutive cardiac cycles,
      displaying an indicator of a cardiac event based on the variation of the trajectory bifurcation, and
      delivering a treatment to the patient based on the indicator of the cardiac event.

2. The system of claim 1, wherein the loop trajectory is a test loop trajectory that comprises a first plurality loop trajectories obtained during a first time period and the control loop trajectory comprises a second plurality of loop trajectories obtained during a second time period that is prior to the first time period.

3. The system of claim 2, wherein the first time period comprises a time period in present or recent past and the second time period comprises a time period in a more distant past.

4. The system of claim 2, wherein the first time period comprises a time period within 60 minutes of a present time and the second time period comprises a time period within 72 hours of the present time.

5. The system of claim 2, wherein the first time period and the second time period are separated by at least 5 minutes.

6. The system of claim 1, wherein the portion of the ECG signal comprises a QRS wave.

7. The system of claim 1, wherein the portion of the ECG signal comprises at least one of a T wave, a P wave and a S wave.

8. The system of claim 1, wherein identifying the trajectory bifurcation further comprises measuring a degree of trajectory bifurcation between the loop trajectory and the control loop trajectory.

9. The system of claim 8, wherein measuring the degree of the trajectory bifurcation is based on a statistical analysis.

10. The system of claim 9, wherein the statistical analysis is a non-Gaussian statistical analysis.

11. The system of claim 1, wherein identifying the trajectory bifurcation further comprises identifying landmarks in the loop trajectory and in the control loop trajectory.

12. The system of claim 1, wherein identifying the trajectory bifurcation further comprises determining a measure of a shape uncertainty of the loop trajectory and the control loop trajectory.

13. The system of claim 12, wherein determining the measure of the shape uncertainty is based on a statistical analysis of an uncertainty boundary of the loop trajectory and the control loop trajectory.

14. The system of claim 1, wherein the cardiac event comprises an impending acute degeneration of a patient's medical condition.

15. The system of claim 14, wherein the impending acute degeneration is one of a cardiac arrest and a traumatic arrest.

16. The system of claim 1, wherein the first computing device comprises a defibrillator.

17. The system of claim 1, wherein the first computing device comprises a mobile computing device.

18. The system of claim 17, wherein the first computing device is configured to transmit the indicator of the cardiac event to a defibrillator.

* * * * *